US012667295B2

(12) United States Patent
Sullivan

(10) Patent No.: US 12,667,295 B2
(45) Date of Patent: Jun. 30, 2026

(54) ECG ANALYSIS OF SIGNALS WITH OFFSETS

(71) Applicant: West Affum Holdings DAC, Dublin (IE)

(72) Inventor: Joseph L. Sullivan, Kirkland, WA (US)

(73) Assignee: West Affum Holdings DAC, Dublin (IE)

( * ) Notice: Subject to any disclaimer, the term of this patent is extended or adjusted under 35 U.S.C. 154(b) by 371 days.

(21) Appl. No.: 18/073,248

(22) Filed: Dec. 1, 2022

(65) Prior Publication Data

US 2023/0172515 A1 Jun. 8, 2023

Related U.S. Application Data

(60) Provisional application No. 63/285,439, filed on Dec. 2, 2021.

(51) Int. Cl.
| | |
|---|---|
| *A61B 5/318* | (2021.01) |
| *A61B 5/308* | (2021.01) |
| *A61N 1/39* | (2006.01) |

(52) U.S. Cl.
CPC .............. *A61B 5/318* (2021.01); *A61B 5/308* (2021.01); *A61N 1/3904* (2017.08)

(58) Field of Classification Search
CPC ...... G16H 50/20; A61B 5/0006; A61B 5/318; A61B 5/7225; A61B 5/308; A61B 5/25; A61B 5/24; A61B 5/28; A61B 5/05; A61B 5/00; Y10S 128/92
See application file for complete search history.

(56) References Cited

U.S. PATENT DOCUMENTS

| | | | |
|---|---|---|---|
| 3,724,455 A | | 4/1973 | Unger |
| 4,291,699 A | | 9/1981 | Geddes et al. |
| 4,565,201 A | * | 1/1986 | Lass ...................... A61B 5/308 |
| | | | 600/509 |
| 4,583,524 A | | 4/1986 | Hutchins |

(Continued)

FOREIGN PATENT DOCUMENTS

| | | |
|---|---|---|
| WO | 9839061 A2 | 9/1998 |
| WO | 2016154425 A1 | 9/2016 |

OTHER PUBLICATIONS

Heartstart MRx and XL AED Algorithm—Application Note, Jul. 2001, Edition 2 Philips Healthcare, USA.

(Continued)

*Primary Examiner* — Deborah L Malamud
(74) *Attorney, Agent, or Firm* — Seed Intellectual Property Law Group LLP

(57) ABSTRACT

An electrocardiogram (ECG) acquisition system comprises a processor configured to process an ECG signal from a patient, a plurality of ECG electrodes configured to be coupled to the patient to obtain the ECG signal from the patient, and an analog-to-digital (A/D) converter configured to acquire the ECG signal from the plurality of ECG electrodes, and to provide the ECG signal to the processor as ECG data representative of the ECG signal. The A/D converter is configured to acquire the ECG signal at a first resolution and the processor is configured to process the ECG data at a second resolution, and the first resolution is higher than the second resolution.

20 Claims, 5 Drawing Sheets

(56) References Cited

U.S. PATENT DOCUMENTS

| | | | |
|---|---|---|---|
| 4,617,938 A | 10/1986 | Shimoni et al. |
| 4,619,265 A | 10/1986 | Morgan et al. |
| 4,895,151 A | 1/1990 | Grevis et al. |
| 4,928,690 A | 5/1990 | Heilman et al. |
| 4,955,381 A | 9/1990 | Way et al. |
| 5,078,134 A | 1/1992 | Heilman et al. |
| 5,228,449 A | 7/1993 | Christ et al. |
| 5,348,008 A | 9/1994 | Bomn et al. |
| 5,353,793 A | 10/1994 | Bomn |
| RE34,800 E | 11/1994 | Hutchins |
| 5,376,104 A | 12/1994 | Sakai et al. |
| 5,381,803 A | 1/1995 | Herleikson et al. |
| 5,394,892 A | 3/1995 | Kenny et al. |
| 5,405,362 A | 4/1995 | Kramer et al. |
| 5,425,749 A | 6/1995 | Adams |
| 5,474,574 A | 12/1995 | Payne et al. |
| 5,554,174 A | 9/1996 | Causey, III |
| 5,601,612 A | 2/1997 | Gliner et al. |
| 5,630,834 A | 5/1997 | Bardy |
| 5,662,690 A | 9/1997 | Cole et al. |
| 5,709,215 A | 1/1998 | Perttu et al. |
| 5,769,872 A | 6/1998 | Lopin et al. |
| 5,782,878 A | 7/1998 | Morgan et al. |
| 5,792,204 A | 8/1998 | Snell |
| 5,803,927 A | 9/1998 | Cameron et al. |
| 5,902,249 A | 5/1999 | Lyster |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,068,651 A | 5/2000 | Brandell |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,351,671 B1 | 2/2002 | Myklebust et al. |
| 6,356,785 B1 | 3/2002 | Snyder et al. |
| 6,427,083 B1 | 7/2002 | Owen et al. |
| 6,529,875 B1 | 3/2003 | Nakajima et al. |
| 6,546,285 B1 | 4/2003 | Owen et al. |
| 6,671,545 B2 | 12/2003 | Fincke |
| 6,681,003 B2 | 1/2004 | Linder et al. |
| 6,694,187 B1 | 2/2004 | Freeman |
| 6,762,917 B1 | 7/2004 | Verbiest et al. |
| 6,941,168 B2 | 9/2005 | Girouard |
| 7,065,401 B2 | 6/2006 | Worden |
| 7,149,576 B1 | 12/2006 | Baura et al. |
| 7,336,994 B2 | 2/2008 | Hettrick et al. |
| 7,379,771 B2 | 5/2008 | Kovac et al. |
| 7,559,902 B2 | 7/2009 | Ting et al. |
| 7,865,238 B2 | 1/2011 | Brink |
| 7,870,761 B2 | 1/2011 | Valentine et al. |
| 7,894,894 B2 | 2/2011 | Stadler et al. |
| 7,974,689 B2 | 7/2011 | Volpe et al. |
| 8,024,037 B2 | 9/2011 | Kumar |
| 8,036,746 B2 | 10/2011 | Sanders |
| 8,135,462 B2 | 3/2012 | Owen et al. |
| 8,140,154 B2 | 3/2012 | Donnelly et al. |
| 8,369,944 B2 | 2/2013 | Macho et al. |
| 8,548,557 B2 | 10/2013 | Garstka et al. |
| 8,615,295 B2 | 12/2013 | Savage et al. |
| 8,644,925 B2 | 2/2014 | Volpe et al. |
| 8,825,154 B2 | 9/2014 | Jorgenson et al. |
| 8,838,235 B2 | 9/2014 | Cowan et al. |
| 8,897,860 B2 | 11/2014 | Volpe et al. |
| 8,904,214 B2 | 12/2014 | Volpe et al. |
| 8,965,500 B2 | 2/2015 | Macho et al. |
| 8,996,101 B2 | 3/2015 | Zhang et al. |
| 9,008,801 B2 | 4/2015 | Kaib et al. |
| 9,089,685 B2 | 7/2015 | Sullivan et al. |
| 9,131,901 B2 | 9/2015 | Volpe et al. |
| 9,132,267 B2 | 9/2015 | Kaib |
| 9,408,548 B2 | 8/2016 | Volpe et al. |
| 9,454,219 B2 | 9/2016 | Volpe et al. |
| 9,533,165 B1 | 1/2017 | Gunderson |
| 9,592,403 B2 | 3/2017 | Sullivan |
| 9,757,579 B2 | 9/2017 | Foshee, Jr. et al. |
| 9,757,581 B2 | 9/2017 | Sullivan et al. |
| 10,016,614 B2 | 7/2018 | Sullivan |
| 10,322,291 B2 | 6/2019 | Medema et al. |
| 11,077,310 B1 | 8/2021 | Sullivan |
| 11,103,717 B2 | 8/2021 | Sullivan et al. |
| 11,160,990 B1 | 11/2021 | Sullivan et al. |
| 11,363,958 B2 | 6/2022 | Nguyen et al. |
| 2003/0158593 A1 | 8/2003 | Heilman et al. |
| 2003/0187479 A1 | 10/2003 | Thong |
| 2004/0049117 A1 | 3/2004 | Ideker et al. |
| 2004/0220623 A1 | 11/2004 | Hess |
| 2004/0230105 A1 | 11/2004 | Geva et al. |
| 2005/0107833 A1 | 5/2005 | Freeman et al. |
| 2005/0107834 A1 | 5/2005 | Freeman et al. |
| 2005/0131476 A1 | 6/2005 | Kim et al. |
| 2006/0017575 A1 | 1/2006 | McAdams |
| 2006/0173364 A1 | 8/2006 | Clancy et al. |
| 2007/0179539 A1 | 8/2007 | DeGroot et al. |
| 2008/0033495 A1 | 2/2008 | Kumar |
| 2008/0208070 A1 | 8/2008 | Snyder et al. |
| 2008/0215103 A1 | 9/2008 | Powers et al. |
| 2008/0306560 A1 | 12/2008 | Macho et al. |
| 2008/0312708 A1 | 12/2008 | Snyder |
| 2008/0312709 A1 | 12/2008 | Volpe et al. |
| 2009/0005827 A1 | 1/2009 | Weintraub et al. |
| 2009/0018595 A1 | 1/2009 | Bharmi et al. |
| 2010/0007413 A1 | 1/2010 | Herleikson et al. |
| 2010/0114248 A1 | 5/2010 | Donofrio et al. |
| 2010/0298899 A1 | 11/2010 | Donnelly et al. |
| 2010/0331904 A1 | 12/2010 | Warren et al. |
| 2011/0022105 A9 | 1/2011 | Owen et al. |
| 2011/0288604 A1 | 11/2011 | Kaib et al. |
| 2011/0288605 A1 | 11/2011 | Kaib et al. |
| 2012/0022355 A1 | 1/2012 | Byrd et al. |
| 2012/0059270 A1 | 3/2012 | Grunwald |
| 2012/0108911 A1 | 5/2012 | Drysdale et al. |
| 2012/0112903 A1 | 5/2012 | Kaib et al. |
| 2012/0144551 A1 | 6/2012 | Guldalian |
| 2012/0150008 A1 | 6/2012 | Lanar et al. |
| 2012/0158075 A1 | 6/2012 | Kaib et al. |
| 2012/0265265 A1 | 10/2012 | Razavi et al. |
| 2012/0277638 A1 | 11/2012 | Skelton et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |
| 2013/0085538 A1 | 4/2013 | Volpe et al. |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0025131 A1 | 1/2014 | Sullivan et al. |
| 2014/0025132 A1 | 1/2014 | Libbus et al. |
| 2014/0070957 A1 | 3/2014 | Longinotti-Buitoni et al. |
| 2014/0150781 A1 | 6/2014 | Capua et al. |
| 2014/0163663 A1 | 6/2014 | Poddar et al. |
| 2014/0324112 A1 | 10/2014 | Macho et al. |
| 2014/0378812 A1 | 12/2014 | Saroka et al. |
| 2015/0037636 A1 | 2/2015 | Amsler et al. |
| 2015/0039053 A1 | 2/2015 | Kaib et al. |
| 2015/0105835 A1 | 4/2015 | Thakur et al. |
| 2015/0265845 A1 | 9/2015 | Sullivan et al. |
| 2015/0297107 A1 | 10/2015 | Sullivan et al. |
| 2015/0328472 A1 | 11/2015 | Sullivan et al. |
| 2016/0000349 A1 | 1/2016 | Sullivan et al. |
| 2016/0004831 A1 | 1/2016 | Carlson et al. |
| 2016/0007877 A1 | 1/2016 | Felix et al. |
| 2016/0015329 A1 | 1/2016 | Kohlrausch et al. |
| 2016/0067514 A1 | 3/2016 | Sullivan |
| 2016/0074667 A1 | 3/2016 | Sullivan et al. |
| 2016/0082277 A1 | 3/2016 | Foshee, Jr. et al. |
| 2016/0121100 A1 | 5/2016 | Crone et al. |

(56) References Cited

U.S. PATENT DOCUMENTS

| | | |
|---|---|---|
| 2016/0235320 A1 | 8/2016 | Sarkar et al. |
| 2016/0278698 A1 | 9/2016 | Freeman et al. |
| 2016/0331984 A1 | 11/2016 | Firoozabadi et al. |
| 2017/0056682 A1 | 3/2017 | Kumar et al. |
| 2017/0157416 A1 | 6/2017 | Medema et al. |
| 2017/0252571 A1 | 9/2017 | Dascoli et al. |
| 2018/0028083 A1 | 2/2018 | Greenhut et al. |
| 2018/0093102 A1 | 4/2018 | Sullivan et al. |
| 2018/0116537 A1 | 5/2018 | Sullivan et al. |
| 2018/0117299 A1 | 5/2018 | Gustavson et al. |
| 2018/0184933 A1 | 7/2018 | Sullivan et al. |
| 2018/0185662 A1 | 7/2018 | Foshee, Jr. et al. |
| 2018/0221648 A1 | 8/2018 | Gustavson et al. |
| 2018/0318593 A1 | 11/2018 | Sullivan |
| 2019/0030351 A1 | 1/2019 | Sullivan et al. |
| 2019/0030352 A1 | 1/2019 | Sullivan et al. |
| 2020/0164217 A1 | 5/2020 | Sullivan |

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.
LIFECOR LifeVest System Model WCD 3100 Operator's Manual, 2006, PN 20B0040 Rev FI, Zoll Lifecor Corporation, Pittsburgh, PA.
LifeVest Model 4000 Patient Manual, Zoll, 2009, PN 20B0047 Rev B.
Pagan-Carlo, et al., "Encircling Overlapping Multipulse Shock Waveforms for Transthoracic Defibrillation," JACC Journals, Dec. 1998, vol. 32 Issue 7, p. 2065-2071.
The LifeVest Network/Patient Data Management System, Zoll, 2015, 2000503 Rev A.

* cited by examiner

ECG ANALYSIS OF SIGNALS WITH OFFSETS

CROSS-REFERENCE TO RELATED APPLICATIONS

The present application claims the benefit of U.S. Application No. 63/285,439 filed Dec. 2, 2021. Said Application No. 63/285,439 is hereby incorporated herein by reference in its entirety.

BACKGROUND

Wearable cardioverter defibrillators (WCDs) analyze patient signals to determine if the patient is experiencing a cardiac arrest. If a ventricular tachycardia/ventricular fibrillation (VT/VF) arrest is suspected, the WCD will alarm to warn the patient and bystanders of an impending shock. If no stop shock signal is received, then the WCD will apply one or more therapeutic shocks to the patient.

WCDs employ analysis of the patient's electrocardiogram (ECG) signals obtained using ECG electrodes attached to the patient's body when wearing the WCD. A processor receives and analyzes the ECG signals as they are received to determine patient parameters such as heart rate and to determine whether the patient is experiencing a cardiac condition that would warrant the application of a therapeutic shock. The ECG signals can be recorded and saved in memory by the WCD system. ECG analysis of long-term recordings can be useful for diagnosing conditions such as atrial fibrillation (AF), runs of ventricular tachycardia (VT), asystolic pauses, and other conditions. ECG acquisition systems can be alternating-current (AC) coupled or direct-current (DC) coupled and can utilize either floating-point arithmetic or fixed-point arithmetic.

DESCRIPTION OF THE DRAWING FIGURES

Claimed subject matter is particularly pointed out and distinctly claimed in the concluding portion of the specification. However, such subject matter can be understood by reference to the following detailed description when read with the accompanying drawings in which:

Figure 1:
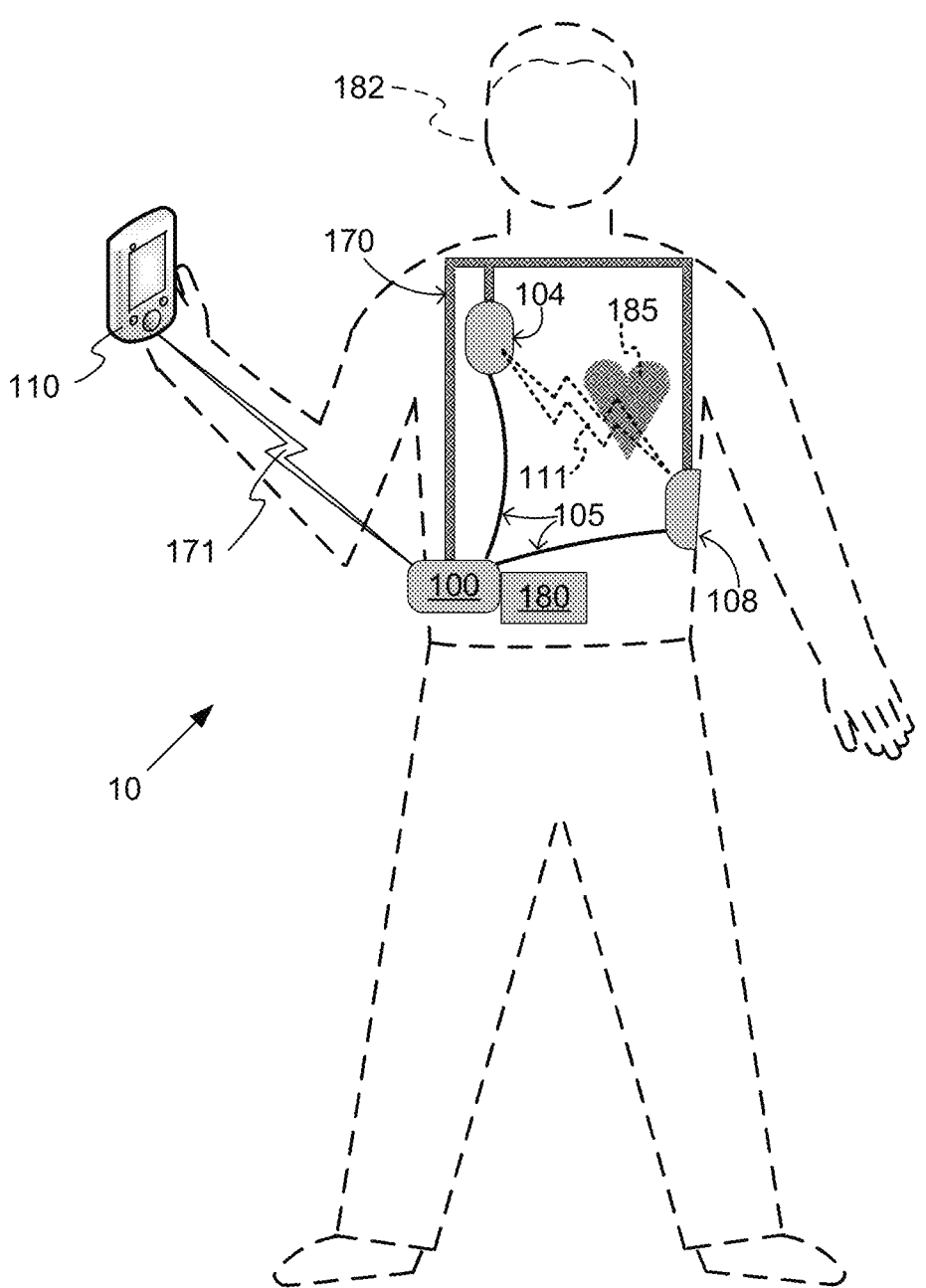
FIG. 1 is a diagram of a WCD system including an external defibrillator in accordance with one or more embodiments.

It will be appreciated that for simplicity and/or clarity of illustration, elements illustrated in the figures have not necessarily been drawn to scale. For example, the dimensions of some of the elements can be exaggerated relative to other elements for clarity. Further, if considered appropriate, reference numerals have been repeated among the figures to indicate corresponding and/or analogous elements.

DETAILED DESCRIPTION

In the following detailed description, numerous specific details are set forth to provide a thorough understanding of claimed subject matter. It will, however, be understood by those skilled in the art that claimed subject matter can be practiced without these specific details. In other instances, well-known methods, procedures, components and/or circuits have not been described in detail.

In the following description and/or claims, the terms coupled and/or connected, along with their derivatives, can be used. In particular embodiments, connected can be used to indicate that two or more elements are in direct physical and/or electrical contact with each other. Coupled can mean that two or more elements are in direct physical and/or electrical contact. Coupled, however, can also mean that two or more elements are not in direct contact with each other, but yet can still cooperate and/or interact with each other. For example, "coupled" can mean that two or more elements do not contact each other but are indirectly joined together via another element or intermediate elements. Finally, the terms "on," "overlying," and "over" can be used in the following description and claims. "On," "overlying," and "over" can be used to indicate that two or more elements are in direct physical contact with each other. It should be noted, however, that "over" can also mean that two or more elements are not in direct contact with each other. For example, "over" can mean that one element is above another element but not contact each other and can have another element or elements in between the two elements. Furthermore, the term "and/or" can mean "and", it can mean "or", it can mean "exclusive-or", it can mean "one", it can mean "some, but not all", it can mean "neither", and/or it can mean "both", although the scope of claimed subject matter is not limited in this respect. In the following description and/or claims, the terms "comprise" and "include," along with their derivatives, can be used and are intended as synonyms for each other.

Referring now to FIG. 1, a diagram of a WCD system including an external defibrillator in accordance with one or more embodiments will be discussed. FIG. 1 depicts components of a WCD system 10 made according to embodiments, as it might be worn by a person 182. A person such as person 182 can also be referred to as patient 182, or wearer 182 since he or she wears the WCD system 10.

The components of the WCD system of FIG. 1 include a generic support structure 170 shown relative to the body of patient 182, and thus also relative to his or her heart 185. Structure 170 could be a harness, a vest, a half-vest, one or more belts, or a garment, and so on, as per the above. Structure 170 could be implemented in a single component, or multiple components, and so on. Structure 170 is wearable by patient 182, but the manner of wearing it is not depicted, as structure 170 is depicted only generically in FIG. 1. Structure 170 can be designed to be worn under the clothes of patient 182 and can be shaped and sized to effectively remain hidden. This can be accomplished by thin materials, design principles that avoid often-exposed areas of a patient's anatomy, such as the neck, upper chest or lower arms, and/or providing an extensive range of sizes and/or adjustability.

A wearable cardiac defibrillator (WCD) system 10 can be configured to defibrillate a patient 182 who is wearing it by delivering electrical charge to the patient's body in the form of an electric shock delivered in one or more pulses. The components of the WCD system 10 of FIG. 1 include a sample external defibrillator 100 made according to embodiments, and sample defibrillation electrodes 104 and 108 which are coupled to external defibrillator 100 via electrode leads 105. In some examples, defibrillator can comprise an energy storage system to store energy to provide a therapeutic shock to patient 182. Defibrillator 100 and defibrillation electrodes 104 and 108 are coupled to support structure 170. Defibrillation electrodes 104 and 108 can be referred to as therapy electrodes. As such, many of the individual components of defibrillator 100 can be therefore coupled to support structure 170. When defibrillation electrodes 104 and 108 make good electrical contact with the body of patient 182, defibrillator 100 can administer, via electrodes 104 and 108, a brief, strong electric pulse 111 through the body. In some examples, defibrillation electrodes can be configured to be in electrical contact with the patient's skin when the patient is wearing the garment or support structure 170 and/or when defibrillator 100 is delivering therapy to the patient. In some examples, defibrillation electrodes 104 and 108 can be in electrical contact with the patient's skin via an intermediate element such as a silver mesh between the defibrillation electrodes 104 and 108 and the patient's skin. Pulse 111, also known as a defibrillation shock or therapy shock, is intended to go through and restart heart 185 in an effort to save the life of patient 182. Pulse 111 can further include one or more pacing pulses, and so on. A defibrillator typically decides whether to defibrillate or not based on an electrocardiogram ("ECG") signal of the patient. Defibrillator 100, however, can defibrillate or not defibrillate also based on other inputs.

In the example of FIG. 1, defibrillator 100 includes additional individual components, as will be described in more detail later in this document. Briefly, these additional components include a power source or energy storage module that is configured to store an electrical charge, a discharge circuit, and one or more processors. In this example, the components also include a communication module that is integrated with the defibrillation unit in a single electronics module, although the communication module can be provided in an electronics module of the WCD system 10 separately from that of the shown defibrillator 100.

In the example of FIG. 1, defibrillator 100 is shown in the front of the patient. In some embodiments, one or more components of a WCD system 10 are preferably ergonomically designed to fit the lumbar region of the body. The lumbar region is sometimes referred to as the lower spine or as an area of the back in its proximity. A component such as an electronics module can be discreetly worn on the body under a patient's clothes when placed in a lumbar pack/carrying case or carried in a common accessory such as a purse or backpack, effectively hiding it in plain sight. Such an electronics module can include one or more components of the WCD system 10.

The components of the WCD system 10 of FIG. 1 also include an action unit 180. Action unit 180 can also be referred to as a hub or an outside monitoring device. Action unit 180 can be a device for patient 182 to exchange information with the WCD system 10. In particular, action unit 180 can have a user interface that is configured to enable patient 182 to read system messages and enter action inputs.

Action unit 180 can be configured to be coupled to support structure 170. In some embodiments, action unit 180 is integrated with the one or more processors in a single electronics module, for example the same electronics module that includes defibrillator 100. In some embodiments, action unit 180 is electrically coupled with the module of defibrillator 100 via a cable, which can be a permanent cable or a Universal Serial Bus (USB), Firewire connection, or similar cable or connector.

For use, patient 182 can reach into their clothes to access action unit 180. In embodiments where a cable is used, patient 182 can bring action unit 180 to a comfortable position for reading the system messages and entering the action inputs. Accordingly, patient 182 can access and control various functions of the WCD system via action unit 180.

According to embodiments, some of the WCD system functions that can be controlled by action unit 180 can instead be controlled by a mobile communication device 110, redundantly or not. In such embodiments, patient 182 carries mobile communication device 110 on their person for typically much of the day. Patient 182 can carry device 110 in a pocket, in a special holder, or even wear it on their wrist. Patient 182 can use device 110 to communicate with the WCD system 10, which is why patient 182 can also be referred to as user 182. Mobile communication device 110 has a user interface that is configured to enable patient 182 to enter inputs that in this document are often called wireless inputs. Wireless communication links can be established and used in embodiments, for exchanging data, voice, and so on. A wireless communication link is also sometimes referred to as "commlink".

In some examples, a mobile communication device such as device 110 can be a custom-made device that is part of the WCD system 10. If made to look substantially like a common, commercially available mobile communication device, it might help preserve the privacy of patient 182 as to the fact that he or she is wearing a medical device, and thus also help preserve their dignity.

Figure 3:
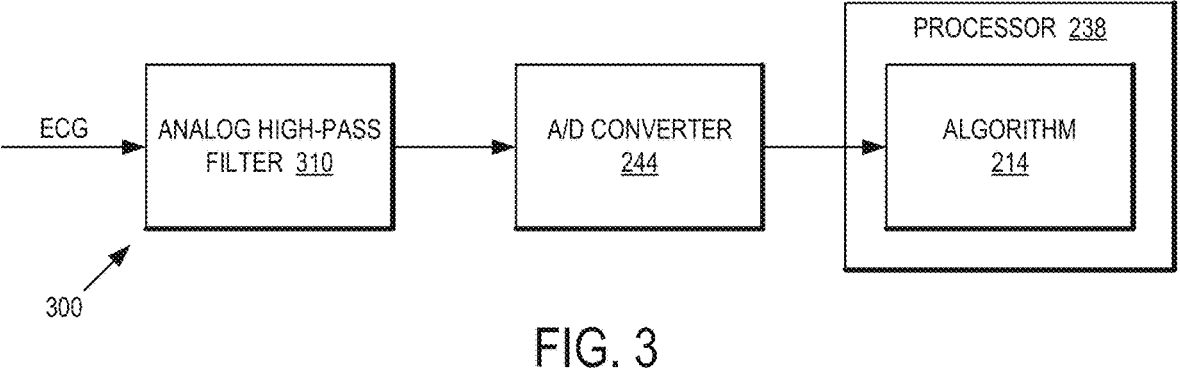
FIG. 3 is a diagram of an AC coupled system for receiving and processing an incoming ECG signal in accordance with one or more embodiments.

Alternately, a mobile communication device such as device 110 can be a wireless telephone, a smartphone, a Personal Digital Assistant (PDA), a personal electronic device, a pager, a laptop computer, a tablet, an e-reader, and so on. It can have an application, or "app", made according to embodiments, so as to perform various functions as described. In such embodiments, mobile communication device 110 can communicate with a wireless service provider network via a remote commlink as shown in FIG. 3 and described with respect to FIG. 3 below. In some examples, a "remote commlink" can refer to a wireless communication link established between devices that are at least 500 feet (150 m) away from each other, and typically farther, such as a cellular communication link. In such instances, the remote commlink can be used for a number of other functions, such as dialing an emergency number (e.g., 911 in the US), which can also be accessible via the mobile communication device 110 directly. In addition, the location of the patient 182 can be determined using Global Positioning System (GPS) for example using appropriate hardware in mobile communication device 110, action unit 180, and/or defibrillator 100. If the WCD system 10 and the mobile communication device 110 have been paired and one of them knows that it is physically close to the other, GPS information can become known and communicated to Emergency Medical Services (EMS) services. The mobile communication device 110 can provide a redundant communication path for the data of the WCD system 10. This redundant communication path might be used as a secondary communication path for remote monitoring data if a primary, in-house internet path is not available for the WCD system 10 to report. The remote commlink can also be used by a remote caregiver to provide patient 182 with troubleshooting assistance, motivational feedback, and so on.

Mobile communication device 110 can thus be configured to establish a local commlink 171 with a communication module of the WCD system 10, which can be inside the same module as defibrillator 100 and/or in action unit 180. If mobile communication device 110 is a wireless telephone or other independent standalone communication device, a local commlink can be established first pursuant to some authentication. Local commlink 171 can be established by the initiative of mobile communication device 110, the communication module, or both. For purposes of this document, a "local commlink" can refer to a wireless communication link established between devices that are at most 50 feet (15 m) away from each other, and typically closer, such as when patient 182 is holding device 110. Local commlink 171 can be a wireless link. Data can be exchanged via local commlink 171, in either direction, or in both directions. In embodiments, local commlink 171 uses radio transmission technology that can be broadband and/or shortwave. Local commlink 171 can use Bluetooth technology, Wi-Fi technology, Zigbee, or other suitable short-range wireless technology.

Figure 2:
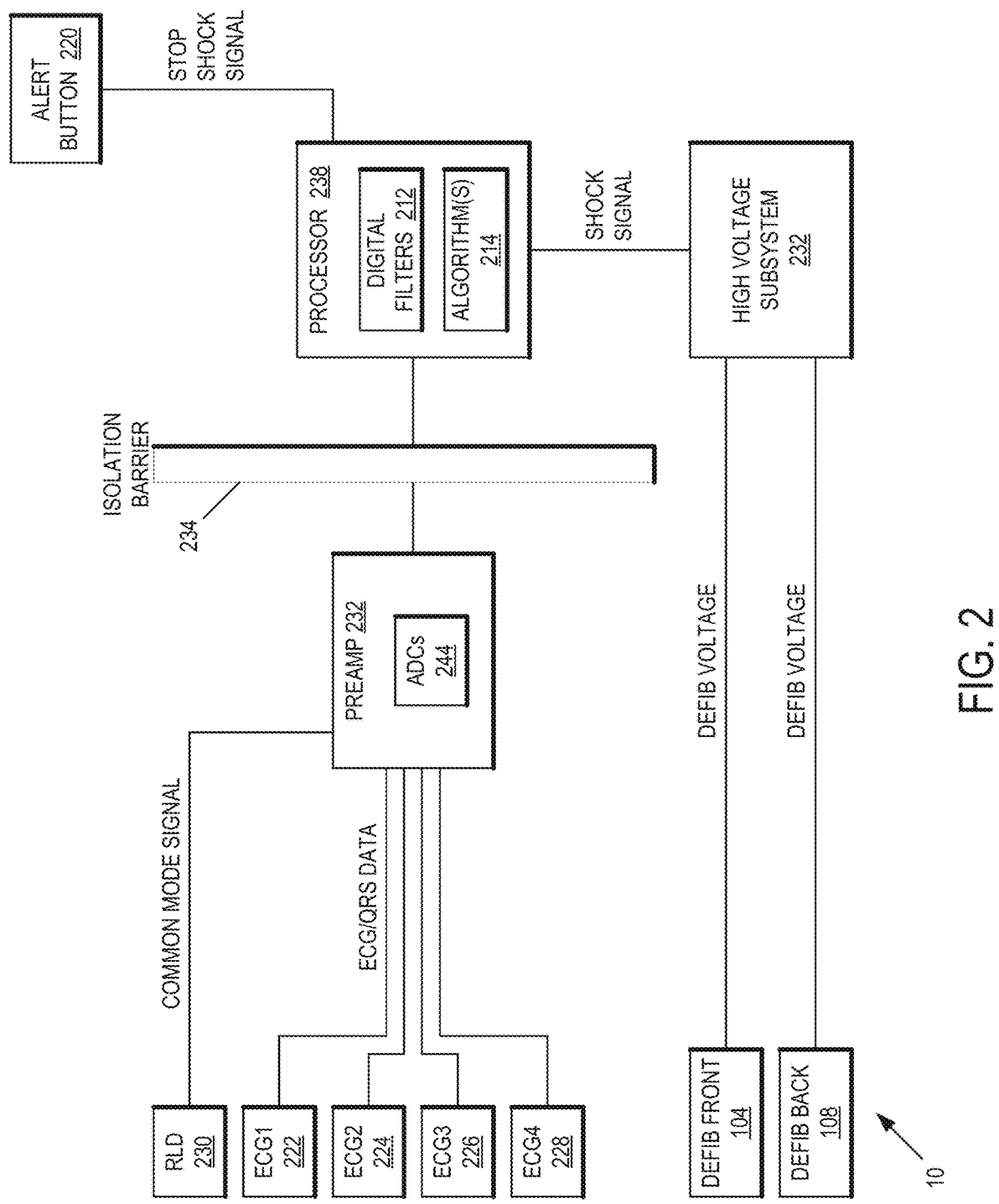
FIG. 2 is a diagram of components of a WCD system in accordance with one or more embodiments.

Referring now to FIG. 2, a diagram of components of a WCD system in accordance with one or more embodiments will be discussed. The WCD system 10 shown in FIG. 2 can be configured to detect ECG and QRS complex signal data detection along with heart rate data detection. In some embodiments, WCD system 10 can comprise a WCD system as shown and described in US Pat. No. 11,160,990 which is incorporated herein by reference in its entirety. The ECG electrodes, ECG1 222, ECG2 224, ECG3 226, and ECG4 228, can comprise silver or silver plated copper electrodes that "dry" attach to the skin of the patient 182. The ECG electrodes provide ECG/QRS data to preamplifier 232. The preamplifier 232 can have a wide dynamic range at its input, for example +/−1.1 V which is much larger than the amplitude of the ECG signals which are about 1 mV. The preamplifier 232 includes one or more analog-to-digital converters (ADCs) 244 to convert the ECG signals into a digital format. A right-leg drive (RLD) electrode 230 can used to provide a common mode signal so that the ECG signals from the ECG electrodes can be provided to preamplifier 232 as differential signals. The digital ECG signals can be provided from the preamplifier 232 to a processor 238, optionally via an isolation barrier 234 which operates to electrically isolate the preamplifier 232 and the ECG signals from the rest of the circuity of WCD system 10.

The processor 238 can be configured to process the digital ECG/QRS data received from the preamplifier 232 with one or more digital filters 212. Since the preamplifier 232 has a wide dynamic range that is much wider than the amplitude range of the ECG signals, digital filters 212 can be utilized to process the ECG/QRS data without concern for clipping of the incoming signals. The wide dynamic range of the preamplifier 232 allows at least most of the ECG filtering to happen in software without the signal being clipped. Digital filters 212 can be effective at removing artifacts from the ECG/QRS data.

In one or more embodiments, the processor 238 can be configured to apply one or more algorithms 214 including for example a rhythm analysis algorithm (RAA) using QRS width information and heart rate data extracted from the digital ECG data using segment-based processing analysis or the QRS width versus heart rate analysis to make a shock or no-shock determination. The RAA algorithm 214 receives the digitized ECG signal and calculates the heart rate and QRS width for each segment. In some examples, the processor 238 can implement one or more algorithms 214 as shown and described in U.S. Pat. No. 11,160,990 which is incorporated herein by reference. The digitized ECG signal is passed over the isolation barrier 234, and the heart rate is derived from the digitized ECG signal. Heart rate and QRS width can be used for making a shock/no-shock decision for each segment, which then can lead to an alarm and a shock. In the event a shockable event is identified, the processor 238 can open a tachycardia episode to start a shock process. Unless the patient 182 provides a patient response using a stop or alert button 220 or other user interface to send a stop shock signal to the processor 238 to intervene before the shock is applied, the processor 238 can send a shock signal to the high voltage subsystem 232 which will apply a defibrillation voltage across the defib front electrode 104 and the defib back electrode 108 to apply one or more therapeutic shocks until there is no longer any shockable event (VT or VF) or until the energy in the high voltage subsystem 232 is depleted.

In one or more embodiments of the WCD system 10, the digital filters 212 coupled with the wide dynamic range of the preamplifier 232 of the ECG circuitry can allow analysis of signals that otherwise would be clipped in systems with a more limited dynamic range. In addition, the filter of the digital filters 212 can highlight complexes similar to the patient's normal rhythm. As a result, artifacts that otherwise may be difficult to discriminate using other methods can be significantly attenuated by the filter. Most ECG monitors use adhesive electrodes, and if the ECG signal is too noisy, then better skin preparation is likely the best remedy. On the contrary, with the WCD system 10 described herein, extreme noise can be tolerated even with using "dry" electrodes, which potentially can be very noisy. Patient motion can cause problems when the "dry" electrodes move relative to the patient's skin which can cause a motion artifact in the ECG. Thus, using filtering techniques, operation of the WCD system 10 would not stop notwithstanding any and all artifacts. Additionally, a filter can be suitable for segment-based ECG processing.

Referring now to FIG. 3, a diagram of an alternating-current (AC) coupled system for receiving and processing an incoming ECG signal in accordance with one or more embodiments will be discussed. As shown in the AC coupled system 300 of FIG. 3, an incoming ECG signal (ECG) can be received at the input of an analog high-pass filter 310. The AC coupled system 300 of FIG. 3 can be understood with respect to the WCD system 10 shown in and described with respect to FIG. 2, and some of the elements of the WCD system 10 of FIG. 2 can be part of or adapted to system 300. ECG acquisition systems such as WCD system 10 of FIG. 2 can be alternating-current (AC) coupled or direct-current (DC) coupled. As shown in FIG. 3, the example AC coupled system 300 can include an analog high-pass filter 310 before the analog-to-digital (A/D) converter 244. This configuration allows A/D converter 244 to have a relatively limited resolution. For example, A/D converter 244 can comprise a 12-bit A/D converter that is capable of representing signals up to +/−20 millivolts (mV) with a 10 microvolt (μV) resolution. For a signal that has been high-pass filtered with analog high-pass filter 310 prior to A/D conversion by A/D converter 244, this signal range can be adequate for typical ECG signals having an amplitude of approximately +/−1 mV. For example, AC coupled system 300 can be employed in a diagnostic ECG system wherein analog high-pass filter 310 is configured to have a 0.05 Hertz (Hz) corner frequency. In another example, AC coupled system 300 can be employed in an ECG monitoring system wherein analog high-pass filter 310 is configured to have a 0.4 Hz corner frequency. In some examples, WCD system 10 can incorporate AC coupled system 300.

In some cases, analog high-pass filter 310 can distort the ECG signal. Such signal distortion potentially can make ECG analysis more difficult, for example where the AC coupled system 300 is employed in an ECG diagnostic system. In addition, the low-frequency information that is removed by analog high-pass filter 310 can be of value to downstream algorithms in some instances, but the low-frequency data is often removed by the analog high-pass filter 310. One way to avoid such signal distortion or signal loss is to utilize a DC coupled system as shown in and described with respect to FIG. 4 below.

Figure 4:
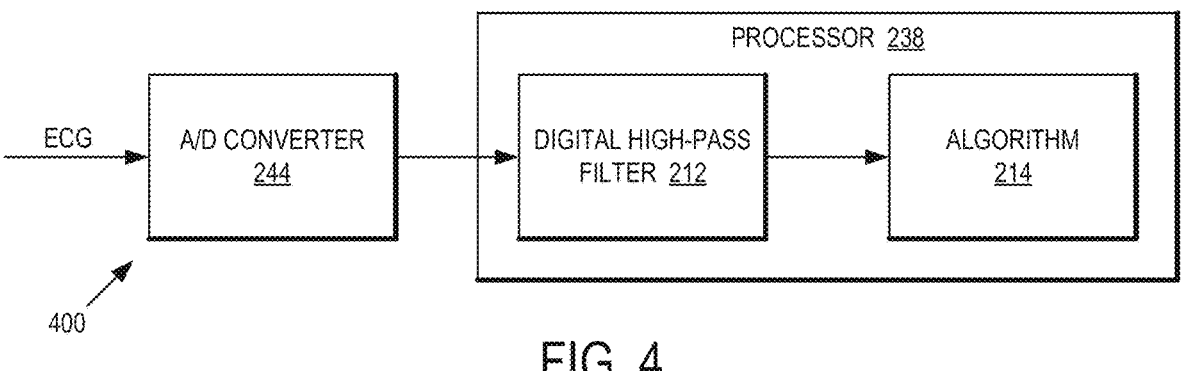
FIG. 4 is a diagram of a DC coupled system for receiving and processing an incoming ECG signal in accordance with one or more embodiments.

Referring now to FIG. 4, a diagram of a direct-current (DC) coupled system for receiving and processing an incoming ECG signal in accordance with one or more embodiments will be discussed. One way to avoid potential signal distortion from the analog high-pass filter 310 as used in AC coupled system 300 is to instead utilize a DC coupled system 400 as shown in FIG. 4. In some examples, electrodes 228 to 230 can be DC coupled between patient 182 and preamplifier 232. In DC coupled system 400, there is no high-pass filter before A/D converter 244. Instead, a digital high-pass filter 212 is used after A/D converter 244. This configuration avoids potential filter distortion from the analog high-pass filter 310, but potential can introduce DC offsets. DC coupled ECG electrodes of a DC coupled system potentially can have ECG offsets that are on the order of hundreds of millivolts. In one example, ff a 12-bit A/D converter is used such as described above for AC coupled system 300, the DC offsets can exceed the dynamic range of the A/D converter 244, causing the signal to be clamped against one of the power supply rails.

In some examples, DC coupled system 400 can avoid signal clamping by configuring or selecting A/D converter 244 to have a relatively high resolution. For example, A/D converter 244 comprise a 24-bit A/D converter such as the ADAS1000 available from Analog Devices., Inc. of Colorado Springs, Colorado, USA. The ADAS1000 comprises a 24-bit A/D converter that can digitize signals up to +/−1.3 volts (V). Using an ADAS1000 as A/D converter 244 can allow the use of DC coupled system 400 while still accommodating the expected range of electrode offsets.

In some examples, using 24-bit data with A/D converter 244 can present some issues because some ECG processing systems can be configured to represent the ECG signal as a 16-bit integer. Performing sixteen-bit integer arithmetic can be relatively simple for processor 238 and can allow ECG filters 212 to be executed efficiently and with lower power consumption. In some cases, however, a 16-bit integer can be inadequate for representing ECG data from A/D converter 244 when A/D converter 244 comprises a 24-bit A/D converter. One example approach to using 24-bit data with a 16-bit ECG processing system is shown in and described with respect to FIG. 5, below.

Figure 5:
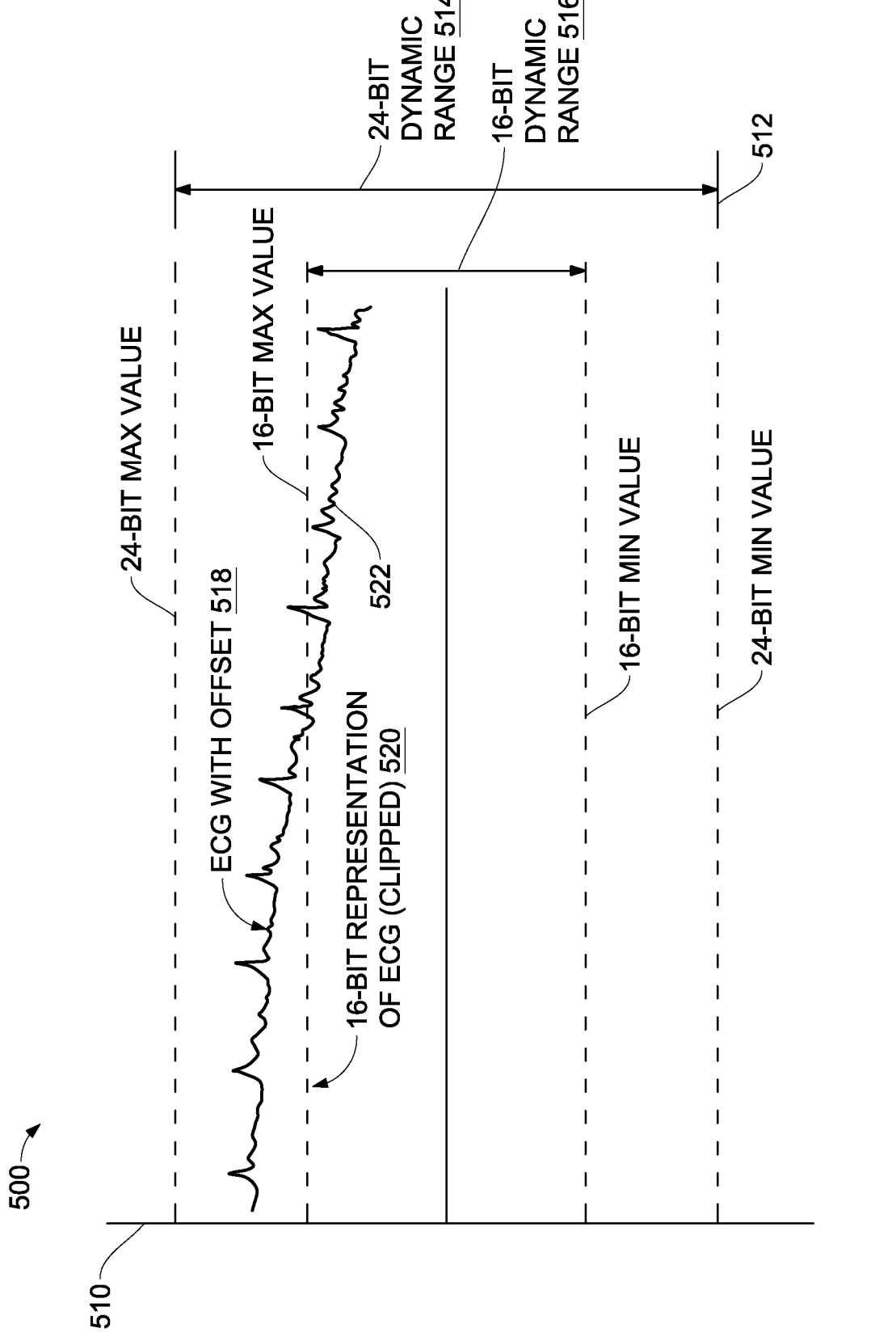
FIG. 5 is a diagram of illustrating the clipping of 24-bit incoming ECG data using a 16-bit system in accordance with one or more embodiments.

Referring now to FIG. 5, a diagram of illustrating the clipping of 24-bit incoming ECG data using a 16-bit system in accordance with one or more embodiments. As shown in graph 500 of FIG. 5, the amplitude of the ECG signal is represented on the vertical axis 510 with respect to time on horizontal axis 512. The 24-bit dynamic range is shown at range ("24-BIT DYNAMIC RANGE") 514 having a maximum value ("24-BIT MAX VALUE") and a minimum value ("24-BIT MIN VALUE"), and the 16-bit dynamic range is shown at range ("16-BIT DYNAMIC RANGE") 516 having a respective maximum value ("16-BIT MAX VALUE") and a respective minimum value ("16-BIT MIN VALUE"). In some examples, one approach to allow 24-bit data to be utilized with a 16-bit system is to simply "clip" the ECG signal any time the signal exceeds the range 516 of the 16-bit data. In the example shown, when the 24-bit value of the ECG signal ("ECG WITH OFFSET") 518 exceeds the value of the 16-bit maximum value, the EGC signal 518 is clipped to the 16-bit maximum value as shown by clipped ECG signal portion ("16-BIT REPRESENTATION OF ECG (CLIPPED)") 520 which is clipped at or limited to the 16-bit maximum value, which results in a horizontal straight line at the maximum 16-bit value for those excess values. Otherwise, the 24-bit value of the signal can be normally represented within the 16-bit dynamic range 516 as shown by ECG signal portion 522. This approach works well when the signal offsets are relatively small. When the offsets exceed the range of the 16-bit data, however, then the ECG signal 518 potentially can be lost. In DC coupled system 400 as shown in FIG. 4, such offsets can persist for long periods of time, which could result in extended periods with no ECG signal.

In accordance with one or more embodiments, 24-bit data can be adapted for use with a 16-bit DC coupled system 400 by implementing a high-pass filter on the 24-bit data and then limiting the data to 16 bits. Such an arrangement is shown in and described with respect to FIG. 6 below.

Figure 6:
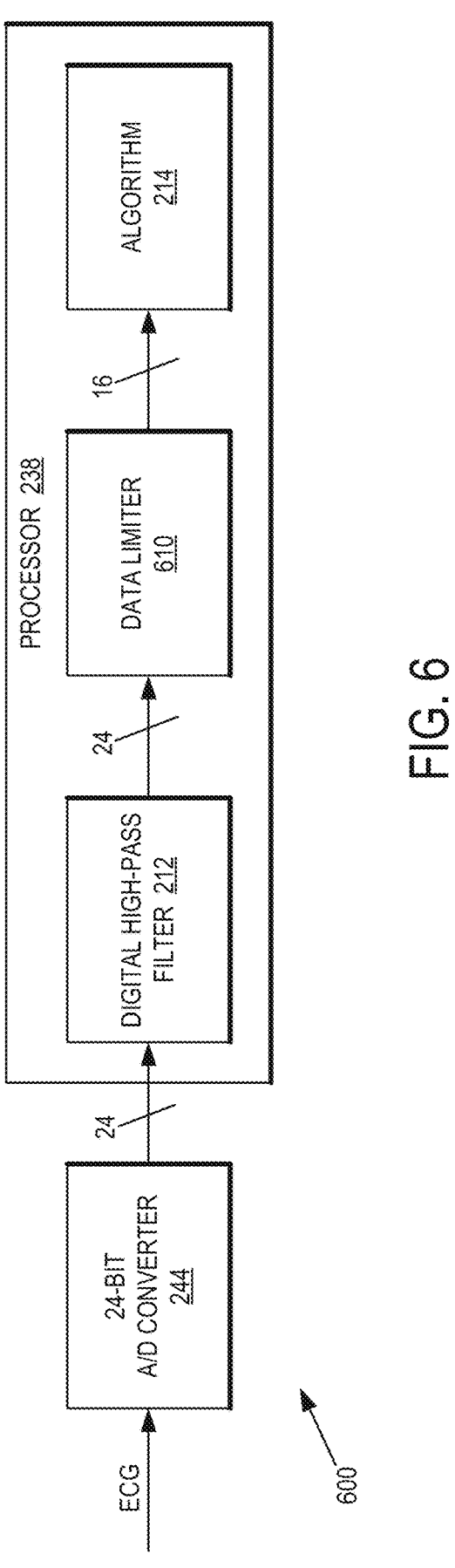
FIG. 6 is a diagram of a 16-bit DC coupled system configured to receive and process 24-bit ECG data in accordance with one or more embodiments.

Referring now to FIG. 6, a diagram of a 16-bit DC coupled system configured to receive and process 24-bit ECG data in accordance with one or more embodiments will be discussed. System 600 as shown in FIG. 6 can provide a DC coupled system that is adapted to utilize 16-bit integer data. In some embodiments, the distortion associated with using an analog high-pass filter such as analog high-pass filter 310 of FIG. 3 can be avoided. In some embodiments, a digital high-pass filter 212 can be implemented, for example using an Infinite Impulse Response (IIR) filter. In other embodiments, digital high-pass filter 212 can be a linear-phase filter such as a Finite Impulse Response (FIR) filter. In other embodiments, digital high-pass filter 212 can be a zero-phase filter or other filter structure. In some examples that employ a linear phase digital filter, distorting the ECG signal can be avoided while still removing the DC component from the ECG signal. In various embodiments, an appropriate filter such as one described above can implemented to remove DC offsets without significantly distorting the ECG for the downstream algorithm 214.

In some embodiments, the corner frequency, or cutoff frequency, of digital high-pass filter 212 can be chosen based on the downstream algorithm 214. For example, algorithm 214 can comprise a diagnostic algorithm that utilizes a corner frequency of 0.05 Hz or lower, while other types of algorithms 214 can utilize corner frequency higher than 0.05 Hz. A higher corner frequency can used for example to remove more baseline wander artifacts, but possibly can introduce signal distortion that may be inappropriate for some systems. As a result, in some embodiments a balance or tradeoff between reducing signal distortion and reducing baseline wander artifacts can be made by selection of an appropriate corner frequency for digital high-pass filter 212, although the scope of the disclosed subject matter is not limited in this respect.

In one or more embodiments, as shown in system 600 of FIG. 6, an ECG signal can be provided to a 24-bit A/D convert 244 to provide 24-bit data to an input of digital high-pass filter 212. The 24-bit output of digital high-pass filter 212 can then be provided to an input of a signal clipper or data limiter 610. Data limiter 610 can operate to replace values exceeding the 16-bit dynamic range with the maximum value, or minimum value as appropriate for negative values, for 16-bit data. In other words, data limiter 610 can replace all values of the 24-bit data that are greater than 32,767 with 32,768, and can replace all values of the 24-bit data that are less than −32,768 with −32,768. This has the effect of limiting or clipping the 24-bit data to or at the maximum or minimum 16-bit data value. In some examples, one count can represent one microvolt (μV), then ECG amplitudes of +/−mV can be represented, which is more than sufficient to avoid signal clipping.

In some embodiments, system 600 can be utilized in any ECG system in which a high-resolution A/D converter such as 24-bit A/D convert 244 is used for signal acquisition but lower-resolution arithmetic for algorithm 214 is desired or employed. It should be noted that although system 600 shown in FIG. 6 shows a 24-bit A/D converter 244 fir signal acquisition and 16-bit arithmetic used for algorithm processing for purposes of example, other systems can utilize the same or similar concept wherein the A/D converter 244 in general is a higher resolution than the resolution of the arithmetic for algorithm 214, and the scope of the disclosed subject matter is not limited in this respect.

Other embodiments include combinations and sub-combinations of features described or shown in the drawings herein, including for example, embodiments that are equivalent to: providing or applying a feature in a different order than in a described embodiment, extracting an individual feature from one embodiment and inserting such feature into another embodiment, removing one or more features from an embodiment, or both removing one or more features from an embodiment and adding one or more features extracted from one or more other embodiments, while providing the advantages of the features incorporated in such combinations and sub-combinations. As used in this paragraph, feature or features can refer to the structures and/or functions of an apparatus, article of manufacture or system, and/or the operations, acts, or modalities of a method.

Although the claimed subject matter has been described with a certain degree of particularity, it should be recognized that elements thereof can be altered by persons skilled in the art without departing from the spirit and/or scope of claimed subject matter. It is believed that the subject matter pertaining to power in a wearable cardioverter defibrillator (WCD) and many of its attendant utilities will be understood by the foregoing description, and it will be apparent that various changes can be made in the form, construction and/or arrangement of the components thereof without departing from the scope and/or spirit of the claimed subject matter or without sacrificing all of its material advantages, the form herein before described being merely an explanatory embodiment thereof, and/or further without providing substantial change thereto. It is the intention of the claims to encompass and/or include such changes.

What is claimed is:

1. An electrocardiogram (ECG) acquisition system, comprising:

a plurality of ECG electrodes configured to be coupled to a patient to obtain an ECG signal from the patient, the ECG signal including a plurality of signal offsets;

an analog-to-digital (A/D) converter configured to acquire the ECG signal from the plurality of ECG electrodes, and to convert the ECG signal into ECG data representative of the ECG signal at a first resolution;

a high-pass filter configured to receive the ECG data from the A/D converter and to high-pass filter the ECG data at the first resolution to remove the plurality of signal offsets; and a processor configured to receive and process the filtered ECG data at a second resolution, wherein the first resolution is higher than the second resolution.

2. The ECG acquisition system of claim 1, wherein:

the high-pass filter is configured to high-pass filter the ECG data at the first resolution prior to processing by the processor at the second resolution.

3. The ECG acquisition system of claim 2, further comprising:

a data limiter configured to receive the ECG data from the high-pass filter after being high-pass filtered and prior to being processed by the processor, wherein the data limiter is further configured to limit the ECG data received from the high-pass filter at the first resolution to a maximum value or a minimum value of the second resolution.

4. The ECG acquisition system of claim 1, wherein:

the high-pass filter has a corner frequency of 0.05 Hz or lower.

5. The ECG acquisition system of claim 1, wherein:

the high-pass filter has a corner frequency greater than 0.05 Hz.

6. The ECG acquisition system of claim 1, wherein:

the high-pass filter has a corner frequency selected to trade off a reduction in signal distortion of the ECG data with a reduction in baseline wander in the ECG data.

7. The ECG acquisition system of claim 1, wherein:

the first resolution comprises a 24-bit resolution, and the second resolution comprises a 16-bit resolution.

8. The ECG acquisition system of claim 1, further comprising:

a preamplifier coupled between the plurality of ECG electrodes and the A/D converter, wherein the plurality of ECG electrodes are direct-current (DC) coupled between the patient and the preamplifier.

9. The ECG acquisition system of claim 1, wherein the ECG acquisition system is incorporated into a wearable system configured to be worn by the patient.

10. The ECG acquisition system of claim 9, wherein the ECG data from the wearable system is remotely monitored and communicated to emergency medical services or a remote caregiver to provide assistance to the patient.

11. The ECG acquisition system of claim 1, wherein the processor is configured to process the ECG signal to detect ventricular fibrillation (VF) or ventricular tachycardia (VT).

12. The ECG acquisition system of claim 1, wherein the ECG data from the ECG acquisition system is transmitted to a communication device.

13. The ECG acquisition system of claim 1, wherein the plurality of ECG electrodes are dry electrodes.

14. The ECG acquisition system of claim 1, wherein the processor is further configured to perform rhythm analysis based on QRS width and heart rate data derived from the ECG data.

15. An electrocardiogram (ECG) acquisition system, comprising:

a plurality of ECG electrodes configured to be coupled to a patient to obtain an ECG signal from the patient, the ECG signal including a plurality of signal offsets;

an analog-to-digital (A/D) converter configured to acquire the ECG signal from the plurality of ECG electrodes, and to convert the ECG signal into ECG data representative of the ECG signal at a first resolution;

a high-pass filter configured to receive the ECG data from the A/D converter and to high-pass filter the ECG data at the first resolution to remove the plurality of signal offsets;

a data limiter configured to receive the ECG data from the high-pass filter, wherein the data limiter is further configured to limit the high-pass filtered ECG data to a maximum value or a minimum value of a second resolution; and a processor configured to receive and process the limited ECG data at the second resolution, wherein the first resolution is higher than the second resolution.

16. The ECG acquisition system of claim 15, wherein:
the high-pass filter has a corner frequency of 0.05 Hz or lower.

17. The ECG acquisition system of claim 15, wherein:
the high-pass filter has a corner frequency greater than 0.05 Hz.

18. The ECG acquisition system of claim 15, wherein:
the high-pass filter has a corner frequency selected to trade off a reduction in signal distortion of the ECG data with a reduction in baseline wander in the ECG data.

19. The ECG acquisition system of claim 15, wherein:
the first resolution comprises a 24-bit resolution, and
the second resolution comprises a 16-bit resolution.

20. The ECG acquisition system of claim 15, further comprising:
a preamplifier coupled between the plurality of ECG electrodes and the A/D converter,
wherein the plurality of ECG electrodes are direct-current (DC) coupled between the patient and the preamplifier.

* * * * *